United States Patent
Warner et al.

(10) Patent No.: US 10,161,909 B2
(45) Date of Patent: Dec. 25, 2018

(54) STEADY STATE FLUID FLOW VERIFICATION FOR SAMPLE TAKEOFF

(71) Applicant: Mustang Sampling LLC, Ravenswood, WV (US)

(72) Inventors: Kevin Warner, The Woodlands, TX (US); Kenneth O. Thompson, Ravenswood, WV (US)

(73) Assignee: Mustang Sampling LLC, Ravenswood, WV (US)

( * ) Notice: Subject to any disclaimer, the term of this patent is extended or adjusted under 35 U.S.C. 154(b) by 225 days.

(21) Appl. No.: 15/297,425

(22) Filed: Oct. 19, 2016

(65) Prior Publication Data
US 2017/0122914 A1 May 4, 2017

Related U.S. Application Data
(60) Provisional application No. 62/248,140, filed on Oct. 29, 2015.

(51) Int. Cl.
| | |
|---|---|
| G01N 1/20 | (2006.01) |
| G01N 29/024 | (2006.01) |
| G01N 1/02 | (2006.01) |
| G01N 29/032 | (2006.01) |
| G01N 29/036 | (2006.01) |

(52) U.S. Cl.
CPC ............. G01N 29/024 (2013.01); G01N 1/02 (2013.01); G01N 29/032 (2013.01); G01N 29/036 (2013.01); *G01N 2291/011* (2013.01); *G01N 2291/015* (2013.01); *G01N 2291/022* (2013.01); *G01N 2291/02836* (2013.01)

(58) Field of Classification Search
CPC ....... G01N 1/02; G01N 1/10; G01N 2001/002
USPC ............................................ 73/64.56, 863.01
See application file for complete search history.

(56) References Cited

U.S. PATENT DOCUMENTS

| | | | |
|---|---|---|---|
| 5,201,581 A * | 4/1993 | Vander Heyden | G01F 1/90 |
| | | | 374/36 |
| 6,512,987 B1 | 1/2003 | Pattern | |
| 6,575,043 B1 | 6/2003 | Huang et al. | |
| 6,758,100 B2 | 7/2004 | Huang | |
| 7,162,933 B2 | 1/2007 | Thompson et al. | |
| 7,484,404 B2 | 2/2009 | Thompson et al. | |
| 7,562,586 B2 | 7/2009 | Rieder et al. | |
| 7,752,919 B2 | 7/2010 | Straub, Jr. et al. | |
| 8,056,399 B2 | 11/2011 | Thompson et al. | |
| 8,360,635 B2 | 1/2013 | Huang et al. | |
| 8,544,343 B2 | 10/2013 | Gottlieb et al. | |
| 8,739,597 B2 | 6/2014 | Day | |

(Continued)

FOREIGN PATENT DOCUMENTS
CN 203274863 U 11/2013

OTHER PUBLICATIONS
International Search Report, PCT/US 16/58139, dated Jan. 26, 2017.

(Continued)

*Primary Examiner* — John Chapman, Jr.
(74) *Attorney, Agent, or Firm* — Cahn & Samuels, LLP

(57) ABSTRACT

A system and method for substantially coincidental sample takeoff flow rate verification which detects unstable flow conditions in a pipeline, terminates fluid sample analysis during flow instability, and resumes sample takeoff when a steady flow state is re-established.

16 Claims, 3 Drawing Sheets

(56) References Cited

U.S. PATENT DOCUMENTS

| | | |
|---|---|---|
| 8,783,088 B2 | 7/2014 | Weaver |
| 9,285,299 B2 | 3/2016 | Thompson |
| 2008/0289427 A1 | 11/2008 | Brandt et al. |
| 2009/0312876 A1 | 12/2009 | Yoneda et al. |
| 2010/0132449 A1 | 6/2010 | Birkett et al. |
| 2015/0000426 A1 | 1/2015 | Rolston et al. |

OTHER PUBLICATIONS

English Translation of CN203274863.
ISO 8943 Refrigerated light hydrocarbon fluids—Sampling of liquefied natural gas—continuous and intermittent methods 2nd ed., 2007.

\* cited by examiner

STEADY STATE FLUID FLOW VERIFICATION FOR SAMPLE TAKEOFF

FIELD OF INVENTION

This invention relates to an improvement providing enhanced reliability of obtained measurements in the field of gas sample analysis. The invention provides substantially coincidental verification of steady state fluid flow during analytical sample takeoff, particularly suitable for use with cryogenic fluids such as liquid natural gas (LNG).

BACKGROUND OF THE INVENTION

Gas quality, quantity, and energy measurement in the context of fuels, particularly in custody transfer from a pipeline or source, requires sample takeoff and conditioning. It is known that variations in sample measurements may be caused, for example, by fluid flow irregularities, component partitioning, and/or phase separation either before or during the sample extraction process. The presence of flow pulsations, non-laminar flow, and extracted sample lag time are some of the recognized problems that undermine sufficient sample flow uniformity to prevent accurate analysis.

Standard sampling practices in the LNG industry, particularly in the context of custody transfer operation, typically are made when the LNG is at specified levels in a static storage container or based on observations of the physical flow state in a pipeline when a stable flow rate is believed to have been achieved. During periods of instability or erratic flow, sample extraction and analysis is typically suspended until acceptable conditions resume. Governing standards for the sampling of liquefied natural gas, such as ISO 8943: 2007, Chapter 7.1 states that sampling should only occur during " . . . that period of time during which the flow rate is sufficiently stable . . . " The standard does not define any particular method to quantify the stated "stable" condition. However, in the absence of a readily apparent problem, the steady state flow determination conventionally is made only after the fact. That is, only after passing through the analyzer and detecting variations in obtained analytical results beyond a permissible threshold does the stability of the sample flow become suspect. Consequently, the validity of the obtained results is problematic and the accuracy of the results for context energy audits in custody transfer or the like often becomes unreliable. Existing systems and apparatus for flow analysis of fluids in pipelines do not address the problem associated with sample takeoff during unstable flow conditions and therefore overlook the resulting problems with measurement/analytical accuracy.

What is needed is a system integrated or associated with sample takeoff equipment for substantially coincidental verification of a steady flow state of the sampled fluid.

SUMMARY OF THE INVENTION

It is an object of the present invention in certain embodiments to provide a system for determining when the flow of fluids through a pipeline take on a substantially stable and steady flow state appropriate for sample extraction and analysis.

It is another object of the invention to provide at least one method of stable flow verification prior to introducing an extracted sample to analytical equipment for conducting sample analysis.

It is another object of the invention in certain embodiments to provide a system and method for improving the accuracy of analytical measurements taken from samples over an extended period of time, which may include periods of sample flow instability.

A further object of the invention in certain embodiments is to provide a technique for detecting sample flow stability at the time of sample extraction for improved quality to sample analysis.

Still another object of the invention in certain embodiments is to discontinue sample takeoff during periods of flow instability.

A further object of the invention in certain embodiments is to provide a system and method for substantially coincidental flow rate verification with sample takeoff from a fluid containing source.

Certain of these and other objects are satisfied by a sample takeoff system for cryogenic fluids in a pipeline comprising: a sample takeoff probe; a power-operated valve associated with said sample takeoff probe for controlling sample takeoff by the probe; and a detector of fluid flow status in the pipeline located proximately to the sample takeoff probe, said detector generating at least one control signal communicated to said power-operated valve to terminate sample takeoff from the pipeline during fluid flow instability.

Still certain objects and others may be satisfied by a fluid pipeline sample takeoff system for substantially coincidental flow rate verification, comprising: a sample takeoff probe; a sound wave detector for detecting the presence of acoustic anomalies generated by at least one unstable flow condition of the fluid in the pipeline and generating a signal representative thereof; a controller for receiving the signal and determining if the signal exceeds a select threshold; and an electro-mechanically actuated valve associated with the sample takeoff probe and in signal communication with the controller, said electro-mechanically actuated valve being operational to terminate fluid sample extraction upon detection of a threshold exceeding signal and to resume fluid sample extraction from the pipeline upon receipt of a signal not exceeding the select threshold and indicative of reestablishment of a substantially steady flow state.

The foregoing and still other objects of the invention are satisfied by a method for selectively actuating fluid sample extraction by a probe from a pipeline, comprising the steps of: detecting flow conditions of a fluid in a pipeline; generating a detection signal corresponding to a detected signal generated by the flow conditions of the fluid in the pipeline; communicating the detection signal to a controller which determines if the signal exceeds a pre-select threshold indicative of fluid flow instability; and causing a solenoid actuated valve to terminate sample fluid extraction from the pipeline upon detection of a threshold exceeding signal and to resume sample fluid extraction upon detection of a signal less than the pre-selected threshold corresponding to substantially steady state fluid flow.

The present invention contemplates steady state flow verification at the front end of the takeoff system, not the back end. In contrast to existing LNG (cryogenic) or NGL (non-cryogenic) sample conditioning and analysis systems, the present invention contemplates pre-analyzer detection of fluid flow stability. Such detection avoids sample flow instability and the concomitantly undesirable variations in obtained results from an analyzer. The present invention also avoids wasting resources and time associated with sample rejection following the detection of variation only after completing sample analysis. In the context of custody transfer energy content auditing, the invention provides an enhanced degree of confidence in the obtained results.

In theory, the invention relies on sensor detection based on the behavior of sound waves of sufficient frequency (acoustic/ultrasonic). At such frequencies, sound waves mechanically propagate efficiently in liquids, less efficiently in gases, and virtually not at all in mixtures of the two. In a substantially uniform liquid of a specific composition, the speed of sound is relatively high and attenuation is substantially less than in gas of a like composition. Consequently, as ascertained by acoustic measurement, the signal generated by a liquid or liquid/gas mixture in a pipeline can be utilized to determine if a stable flow exists within the pipeline for sample extraction. When sample extraction occurs during steady/stable flow of the sampled stream, more accurate and reliable results are obtained and the requirements of ISO 8943:2007 are achieved.

In one arrangement contemplated by the invention, an acoustical sensor is mounted (either permanently or removably) at or near a sample takeoff probe on a pipeline, for example an LNG transfer. The sensor may be wetted (in contact with the fluid) or placed external to the process, for example, clamp-on. The sensor is in signal communication through an appropriate connection to a sound wave processor/electronic analysis device for measuring one or a combination of the following six characteristics:

A. The speed of sound of an ultrasonic signal through the fluid (active measurement): In the case of LNG, the speed of sound is a function of its temperature, pressure, and composition. It is not a function of the LNG's velocity through the pipeline (i.e. flow rate). Any detected variation in the speed of sound is an indication that at least one of these characteristics (i.e. temperature, pressure, or composition) of the LNG is changing during the timeframe of the measurement and indicates sample instability.

B. The attenuation of the ultrasonic signal through the fluid (active measurement): In the case of LNG, the ultrasonic attenuation coefficient again is strictly a function of its temperature, pressure, and/or composition. A detected variation of signal strength propagating through a known LNG quantity is an indication of an unstable flow state.

C. The change in frequency components of the ultrasonic signal having passed through the fluid (active measurement): As is the case with sound speed and attenuation, a frequency shift in a detected ultrasonic pulse traveling through a known quantity of LNG is indicative of flow instability.

D. The amplitude and frequency spectrum of the mechanical energy generated by the flowing LNG (passive measurement): Flowing liquids in pipelines generate specific levels and frequencies of acoustic energy, or noise. Acoustic or ultrasonic sensors can measure the characteristics of the mechanical energy by passively 'listening'. Changes to the noise generated by flowing LNG within a pipeline are indicators of unstable flow.

E. The physical level of liquid flowing in the pipeline: An ultrasonic signal may be used to determine the level of liquid in the pipeline by detecting the liquid/gas interface, due to the measured reflection through the liquid. A variation in the detection level is a direct indicator that the flow rate is unstable.

F. The physical level of gas flowing in the pipeline: An ultrasonic signal may be used to determine the gas or vaporized liquid level in the pipeline by detecting the liquid/gas interface due to the measured reflection through the gas/vapor. A variation in the detection level is a direct indicator that the flow rate is unstable.

The invention contemplates a diagnostic tool that effectively limits sample takeoff to times when appropriate sample flow conditions exist, for example the presence of a steady flow state. The system monitors flow in the pipeline at or closely proximate to the time of takeoff of a sample, which is then directed to an associated sample conditioner. The invention features takeoff valving triggered to terminate sample takeoff upon detection of a flow variation beyond an allowable threshold and to restart sample takeoff upon resumption of a steady flow state. To this end, the present invention, in one embodiment, recognizes the presence of an appropriate detection flow state window based on attenuation coefficients derived from signal propagation through the pipeline source of the sampled/extracted fluid.

Another embodiment starts with a basic assumption of using ultra-sound to ascertain the propagation of sound waves through the pipeline. A passive embodiment, in theory "listens" to the noise in the pipeline with an external sensor mounted thereon near the extraction probe and generates a baseline of noise under nominal flow conditions. Variations of the noise characteristics beyond an established threshold will trigger an alarm signal and/or automatic shutoff of sample extraction until the baseline is re-established. In other words, if the noise level is outside the threshold boundary during the transfer process, there is an indication of flow disruption caused by irregularities, e.g., bubbles, cavitation, pulsation (from pumping), vapor formation, fluid composition changes from component partitioning, etc. In the presence of such conditions, direct detection of the anomaly prevents introduction of the compromised fluid to the downstream conditioning equipment and gas analyzer.

Particular terminology used herein is for the purpose of describing particular embodiments only and is not intended to be limiting of the invention.

As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

For definitional purposes and as used herein "connected" includes physical attachment, whether direct or indirect, permanently affixed or adjustably mounted, as for example, the vaporizer is connected to the takeoff probe. Thus, unless specified, "connected" is intended to embrace any operationally functional connection.

References to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein.

As used herein, "integrated" and "integral" is intended to connote at least two cooperative, separable, discrete components being combinable into or mated/combined into a single integrated structure.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

As used herein, "power-operated valve" contemplates an automatically operated valve actuated by any of electrical, hydraulic, or pneumatic energy and, more preferably, an electro-mechanically actuated valve such as a solenoid valve.

As used herein, "unitary" is intended to connote an indivisible/undivided single structure.

In the following description, reference is made to the accompanying drawings, and which are shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION OF THE DRAWINGS

Figure 1:
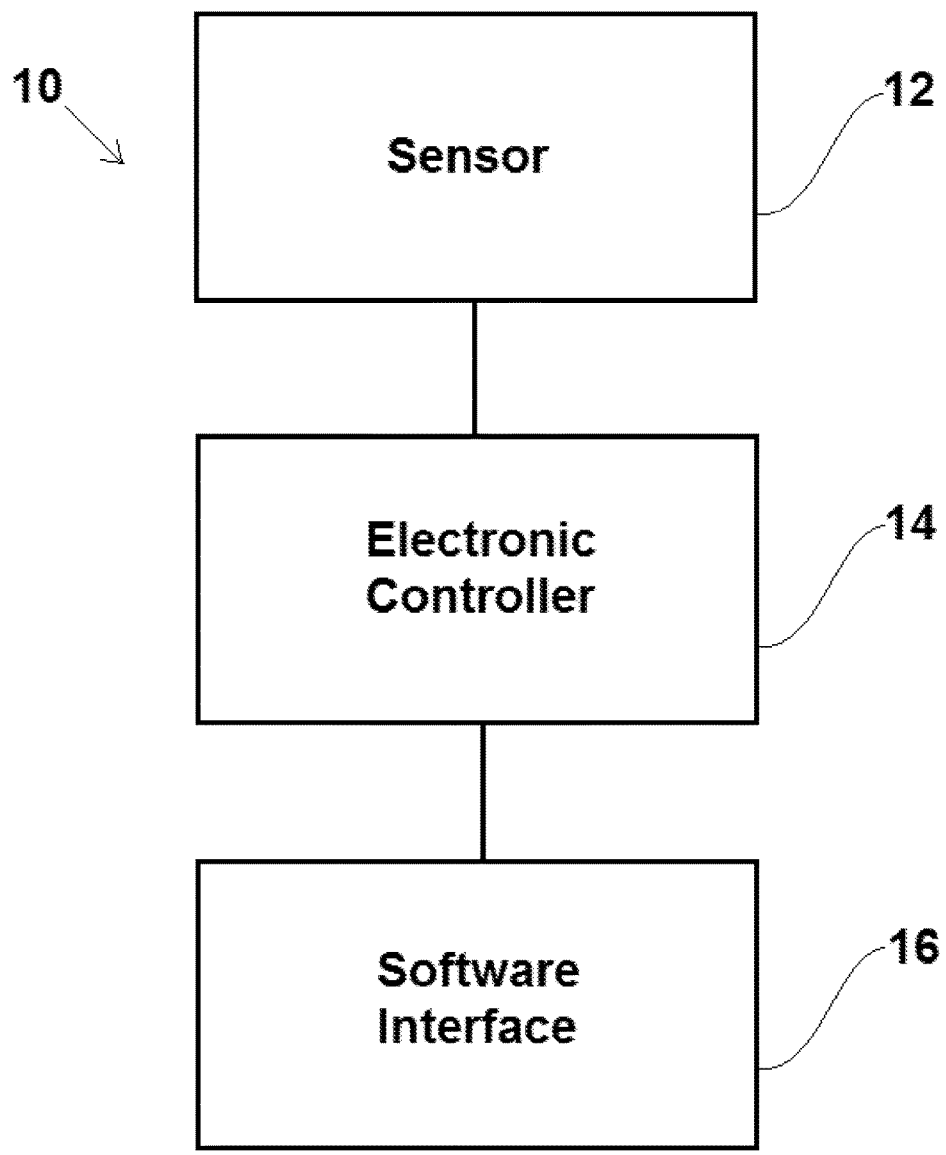
FIG. 1 is a schematic of the basic components of the invention.
Figure 2:
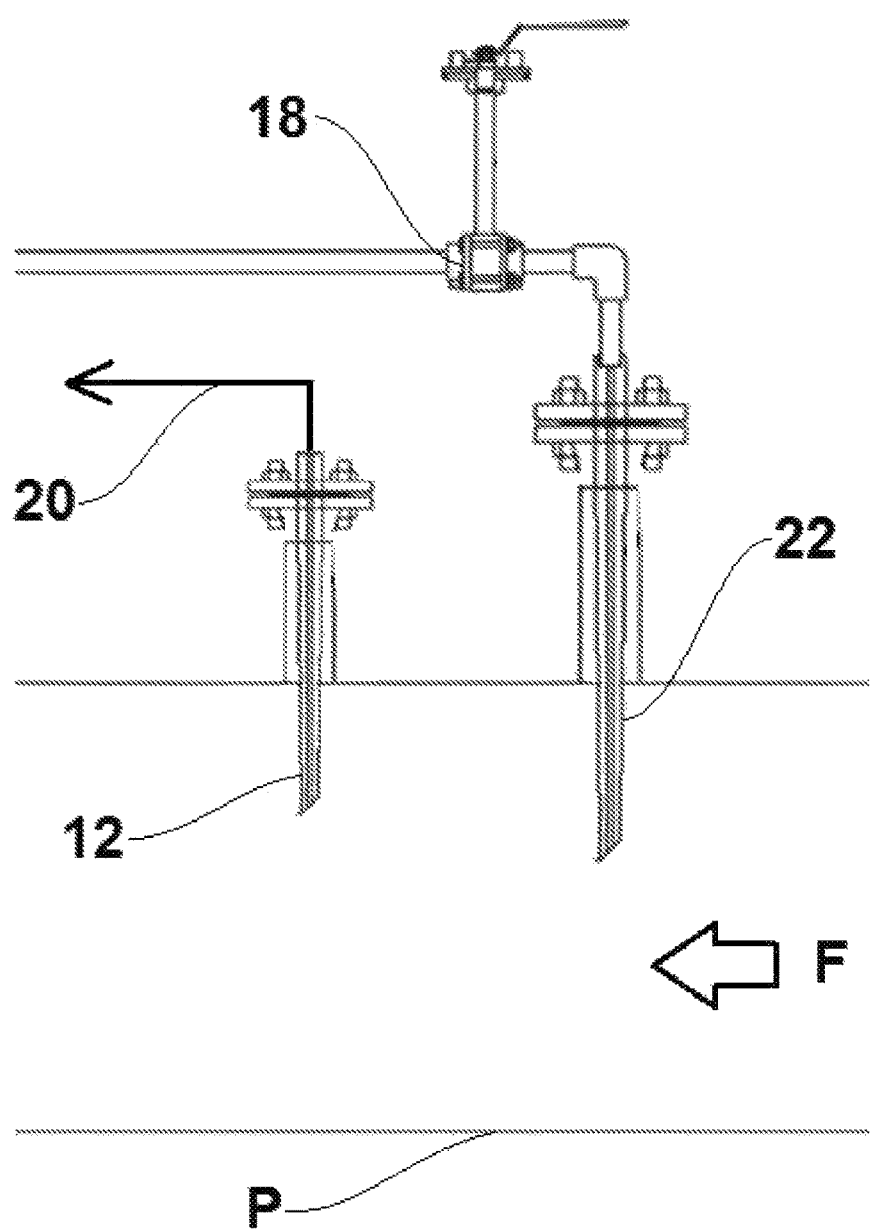
FIG. 2 illustrates an embodiment of the invention where the flow sensor is positioned in the pipeline proximate to the sample takeoff probe.

FIG. 1 illustrates in schematic form, an embodiment of the inventive Steady-State-Flow (SSF) detection system 10. At a most fundamental level, the SSF system 10 of the invention comprises a detection system having a sonic sensor 12 mounted into a flowing stream of cryogenic fluid F (illustrated in FIG. 2), an electronic controller 14, which energizes and measures signals from the sensor 12, and an expert software system 16 to configure and communicate with the controller 14. The controller 14 is connected to a shutoff solenoid valve 18 that terminates sample takeoff when flow instability is detected.

In ordinary operation, the ultrasonic measurement system is affixed to the pipeline P. Typically, if active, the array will include an ultrasonic transmitter and an ultrasonic receiver. If passive, only a sound detector is necessary. In either case, the system 10 is preferably connected electronically to a microchip or PLC for receiving the incoming signal 20, processing the signal according to the selected protocol/algorithm, detecting variations beyond a permitted threshold, generating a signal responsive to the detected variation for appropriate action, i.e., closing a solenoid controlled valve 18 to terminate sample takeoff, generating an alarm, etc. Only upon resumption of a steady flow state would sample takeoff be re-established.

The particular form of the sensor 12 would depend upon the desired functionality of the unit, which is contingent on the selected technique or combinations thereof for active or passive measurements. Regardless of the selected parameter or parameters utilized for steady state flow determination (i.e., ultrasonic wave propagation, ultrasonic wave attenuation, ultrasonic wave boundary reflection, passive noise detection, etc.), the sensor 12 is preferably in connection with a solenoid valve 18, associated with the probe 22 and intermediately disposed in-line between the probe 22 and the down-stream sample analyzer, to be opened during a substantially steady flow state.

The sensor 12 may be in the form of a stand-alone detector (passive) or a wave source generator/transmitter and receiver (active) either in a unitary housing (reflection) or diametrically separated. The sensor 12 may be set in a permanently affixed mounting on a pipeline P, selectively positionable using a clamping array or even temporarily mounted using a flexible belt for easy placement and removal. Preferably, the sensor 12, whether in unitary form or having separate transmitter/receiver elements, is located proximate to an associated sample takeoff probe 22 on the pipeline P to facilitate substantially co-incident flow verification of pipeline fluids F, as illustrated by the embodiment in FIG. 2.

In the context of operation, using a combination of the foregoing approaches and even relying on different sensing functionalities, for example, direct (speed of sound/attenuation coefficient and frequency change/delta) or indirect (noise detection from cavitation/bubbles), can minimize potential inaccuracies arising from flow irregularities of a cryogenic fluid F, like LNG, when the conditions (temperature/pressure) are near the fluid's phase boundary.

Figure 3:
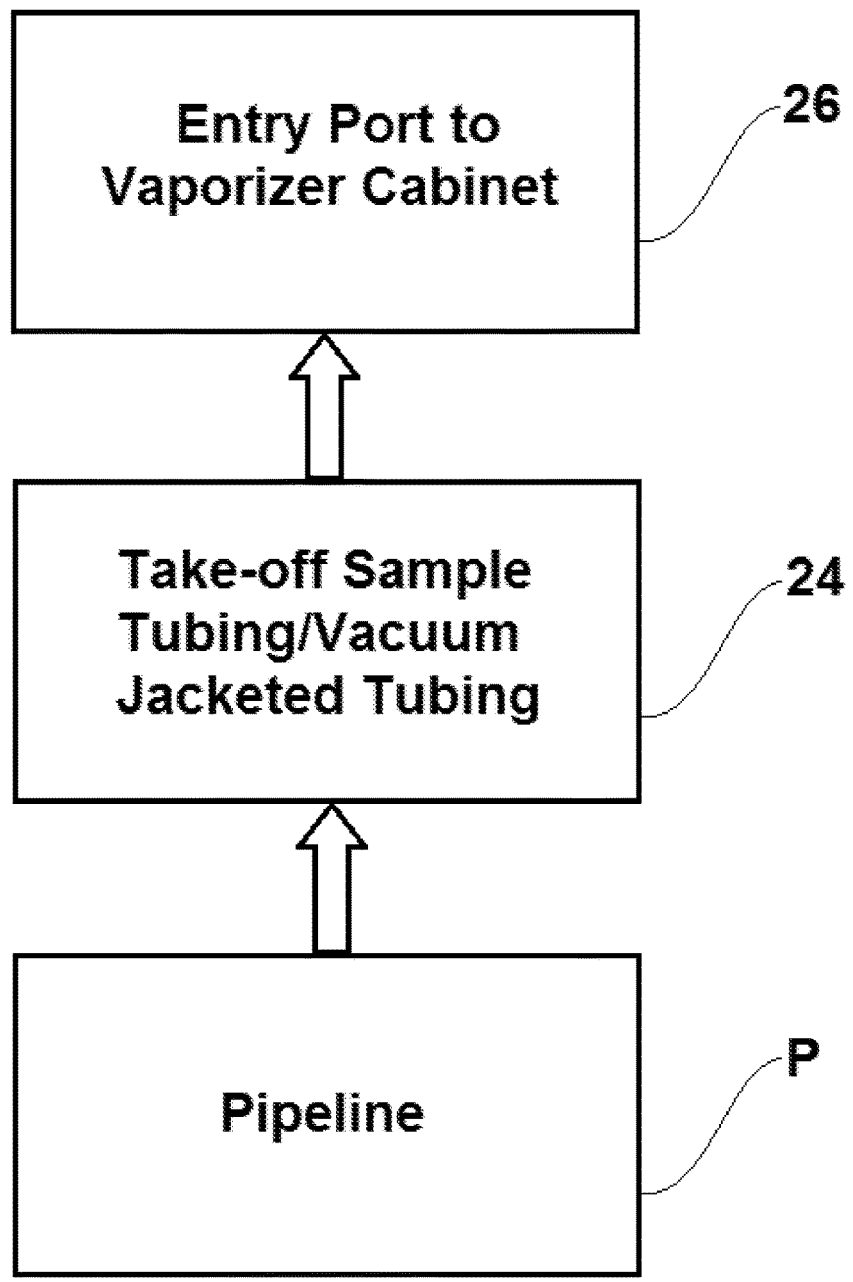
FIG. 3 schematically represents alternative potential embodiments of the invention where the flow sensor is disposed in at least one of three different locations within the sampling system.

FIG. 3 illustrates alternative potential embodiments of the invention where the sensor 12 is at different locations within the sampling system. These include within the pipeline P, which comprises the arrangement depicted in FIG. 2. Alternatively, the sensor 12 may be positioned "downstream" of the takeoff, as for example in the takeoff sample tubing 24 for communicating the sample from the pipeline P to the sample conditioning cabinet, which preferably provides a thermal insulating capability by employing vacuum jacketed tubing or the like. A sensor 12 can also be placed in a passive housing that the sample is passed through following takeoff, such as an unheated PONY® box.

The further option for sensor placement in accordance with the invention is to dispose the sensor 12 at the entry port into the vaporizer cabinet 26 to sense the sample flow state prior to sample conditioning.

In the context of the sample take-off control, so long as the power-operated valve is substantially immediately actuable to open and close dependent upon pipeline flow conditions, while preferably a conventional electromechanical solenoid valve, the valve may be based on other known sources of motive force such as hydraulic, fluidic, or pneumatic systems that can actuate valve shutoff upon detection of flow instability by a connected sensor.

Although selected embodiments of the invention have been described in the forgoing specification, it is understood by those skilled in the art that many modifications and embodiments of the invention will come to mind to which the invention pertains, having benefit of the teaching presented in the foregoing description and associated drawing. It is therefore understood that the invention is not limited to the specific embodiments disclosed herein, and that many modifications and other embodiments of the invention are intended to be included within the scope of the invention. Moreover, although specific terms are employed herein, they are used only in a generic and descriptive sense, and not for purposes of limiting the description of the invention.

We claim:

1. A sample takeoff system for cryogenic fluids in a pipeline comprising:
    a) a sample takeoff probe;
    b) a power-operated valve associated with said sample takeoff probe for controlling sample takeoff by the probe; and
    c) a detector, said detector being a sonic sensor of fluid flow status in the pipeline located proximately to the sample takeoff probe, said detector generating at least one control signal communicated to said power-operated valve to terminate sample takeoff from the pipeline during fluid flow instability.

2. The sample takeoff system of claim 1 further comprising an electronic controller for receiving the communicated signal from the detector and the power operated valve being an electrically actuated solenoid valve.

3. The sample takeoff system of claim 1 where the detector senses sound waves in the frequency range selected from the group consisting of ultrasonic, audible, and infrasonic to monitor pipeline fluid flow status.

4. The sample takeoff system of claim 3 where the detector senses fluid flow instability in the pipeline beyond a permissible threshold from anomalies generated by any of pulsations, phase transitions, and non-laminar flow.

5. The sample takeoff system of claim 4 where the detector is passive, mounted externally on the pipeline, provides a baseline signal corresponding to noise generation at nominal flow conditions associated with flow uniformity and communicates a signal upon detecting noise at a select threshold exceeding the baseline signal.

6. The sample takeoff system of claim 5 where the detector is associated with an ultrasonic wave source generator.

7. The sample takeoff system of claim 6 where the detector measures fluid flow by one of ultrasonic wave propagation, ultrasonic wave attenuation or ultrasonic wave boundary reflection.

8. The sample takeoff system of claim 7 where the ultrasonic wave source generator is diametrically separated from the detector on the pipeline.

9. A fluid pipeline sample takeoff system for substantially coincidental flow rate verification, comprising: a sample takeoff probe; a sound wave detector for detecting the presence of acoustic anomalies generated by at least one unstable flow condition of the fluid in the pipeline and generating a signal representative thereof; a controller receiving the signal and determining if the signal exceeds a select threshold; and an electro-mechanically actuated valve associated with the sample takeoff probe and in signal communication with the controller, said electro-mechanically actuated valve operational to terminate fluid sample extraction upon detection of a threshold exceeding signal and to resume fluid sample extraction from the pipeline upon receipt of a signal not exceeding the select threshold and indicative of reestablishment of a substantially steady flow state.

10. The fluid pipeline sample takeoff system of claim 9 further comprising an ultrasonic transmitter for transmitting an ultrasonic signal into the fluid for analysis of fluid flow selected from the group consisting of ultrasonic wave propagation, ultrasonic wave attenuation and ultrasonic wave boundary attenuation.

11. The fluid pipeline sample takeoff system of claim 9 further comprising an ultrasonic transmitter fixed on the exterior of the pipeline diametrically opposed to the sound wave detector.

12. A method for selectively actuating fluid sample extraction by a probe from a pipeline, comprising the steps of:
    detecting flow conditions of a fluid in a pipeline;
    generating a detection signal corresponding to a detected signal generated by the flow conditions of the fluid in the pipeline where pipeline flow condition signal is based on sonic detection of an acoustical signal in the range selected from the group consisting of ultrasonic, audible, and infrasonic;
    communicating the detection signal to a controller which determines if the signal exceeds a pre-select threshold indicative of fluid flow instability; and
    causing a power operated valve to terminate sample fluid extraction from the pipeline upon detection of a threshold exceeding signal and to resume sample fluid extraction upon detection of a signal less than the pre-selected threshold corresponding to substantially steady state fluid flow.

13. The method of claim 12 where the sonic detection is passive.

14. The method of claim 12 further comprising the step of transmitting an ultrasonic signal into the fluid and detecting the reflected signal generated thereby.

15. The method of claim 12 where the power operated valve is a solenoid valve which is actuated to close and terminate sample takeoff upon detection of a threshold exceeding signal.

16. The method of claim 12 further comprising the step of conveying the sample fluid extracted from the pipeline to an associated analyzer when the signal does not exceed the pre-select threshold indicative of fluid flow instability.

* * * * *